(12) United States Patent
Venuto, Sr.

(10) Patent No.: US 6,673,097 B1
(45) Date of Patent: Jan. 6, 2004

(54) TANNING BOOTH HAVING REDUCED TANNING TIME

(75) Inventor: Ralph Venuto, Sr., Blackwood, NJ (US)

(73) Assignee: Hollywood Tanning Systems, Inc., Mt. Laurel, NJ (US)

( * ) Notice: Subject to any disclaimer, the term of this patent is extended or adjusted under 35 U.S.C. 154(b) by 29 days.

(21) Appl. No.: 09/836,543

(22) Filed: Apr. 18, 2001

Related U.S. Application Data
(60) Provisional application No. 60/270,596, filed on Feb. 23, 2001.

(51) Int. Cl.[7] ................................................. A61N 5/00
(52) U.S. Cl. ............................. 607/91; 607/89; 607/94
(58) Field of Search ............................. 607/88, 89, 94, 607/90, 91; D24/210

(56) References Cited

U.S. PATENT DOCUMENTS

| | | | | |
|---|---|---|---|---|
| 1,583,420 | A | * 5/1926 | Picard | ........................... 607/91 |
| 3,932,151 | A | 1/1976 | Lau | |
| 4,064,995 | A | * 12/1977 | Bustos | ........................ 108/193 |
| 4,065,885 | A | * 1/1978 | Blick et al. | ..................... 4/460 |
| 4,095,113 | A | * 6/1978 | Wolff | ....................... 250/494.1 |
| 4,100,415 | A | * 7/1978 | Blaisdell et al. | ........ 250/455.11 |
| 4,231,289 | A | 11/1980 | Domicent | |
| D268,054 | S | * 2/1983 | Charette | ....................... D24/39 |
| 4,469,102 | A | * 9/1984 | Fish | ......................... 250/494.1 |
| 4,469,951 | A | * 9/1984 | Coco et al. | ............. 250/454.11 |
| 4,660,561 | A | * 4/1987 | Nielsen | ........................ 248/325 |
| 4,832,943 | A | 5/1989 | Grollier et al. | |
| 5,089,269 | A | 2/1992 | Noda et al. | |
| 5,102,660 | A | 4/1992 | Forestier et al. | |
| 5,153,174 | A | 10/1992 | Band et al. | |
| 5,241,958 | A | * 9/1993 | Noeldner | ....................... 4/541.4 |
| 5,268,166 | A | 12/1993 | Barnett et al. | |
| 5,273,214 | A | 12/1993 | Huffstutler | |
| 5,460,192 | A | 10/1995 | McClain | |
| 5,546,678 | A | * 8/1996 | Dhaemers | ..................... 34/224 |
| 5,664,593 | A | 9/1997 | McClain | |
| 5,673,522 | A | * 10/1997 | Schilham | ....................... 174/50 |
| 5,683,437 | A | * 11/1997 | Doty | ............................. 607/88 |
| 5,816,000 | A | * 10/1998 | Izatt et al. | ..................... 160/135 |
| 5,922,333 | A | 7/1999 | Laughlin | |
| 5,971,598 | A | * 10/1999 | Baba et al. | .................. 250/372 |
| 6,052,958 | A | * 4/2000 | Miedema et al. | .............. 52/239 |
| 6,199,557 | B1 | 3/2001 | Laughlin | |
| 6,251,374 | B1 | 6/2001 | Laughlin | |
| 6,298,862 | B1 | 10/2001 | Laughlin | |
| 6,305,384 | B2 | 10/2001 | Laughlin | |
| 6,387,081 | B1 | 5/2002 | Cooper | |
| 6,416,747 | B1 | 7/2002 | Laughlin | |

(List continued on next page.)

FOREIGN PATENT DOCUMENTS

WO     WO 94/12146     6/1994

OTHER PUBLICATIONS

Binks, Training Division, TD49–2R–4, "Spray Application Processes," 4 pp.

*Primary Examiner*—Derek Boles
(74) *Attorney, Agent, or Firm*—Blank Rome LLP

(57) ABSTRACT

A tanning booth generally has rectangular wall panels, a floor frame, a ceiling frame and a fan that is mounted to the ceiling. The wall panels are interconnected in the shape of a figure-8 in order to form a front section or room defined by front wall panels and a back section or room defined by back wall panels. In use, the front room is a changing area that provides privacy for the user to dress and undress, and the back room is the tanning area. An inside door is provided to separate the front room from the back room. The front section and the back section are each hexagonal-shaped rooms that together form the rough figure-8 shape. Tanning lamps are provided to surround the user in the tanning room. The floor has a pattern of holes that permit air to be drawn through the tanning room by a fan mounted on the ceiling to sufficiently cool the user and lamps during tanning.

34 Claims, 9 Drawing Sheets

U.S. PATENT DOCUMENTS

| | | |
|---|---|---|
| 2001/0029961 A1 | 10/2001 | Laughlin |
| 2002/0000236 A1 | 1/2002 | Laughlin |
| 2002/0000237 A1 | 1/2002 | Laughlin |
| 2002/0005208 A1 | 1/2002 | Laughlin |
| 2002/0040721 A1 | 4/2002 | Laughlin |
| 2002/0088475 A1 | 7/2002 | Laughlin |

* cited by examiner

TANNING BOOTH HAVING REDUCED TANNING TIME

RELATED APPLICATIONS

This application claims priority from U.S. application Ser. No. 60/270,596, filed Feb. 23, 2001.

BACKGROUND OF THE INVENTION

1. Field of the Invention

The present invention relates to a tanning booth. More particularly, the present invention relates to an improved tanning booth that is has a design that enables tanning in less than eight minutes and is easy to install.

2. Description of the Related Art

Tanning booths have been developed with tanning lamps, so that a user can obtain and maintain a tan all year round, regardless of weather conditions. Tanning booths have proven to be a healthy and effective, and federal guidelines have been established to ensure that tanning booths continue to be safe. Tanning booth technology continues to improve. However, it is a goal to provide a quality tan in a reduced amount of time in order to be convenient for users as well as to increase the value of the tanning booth by being able to accommodate a greater number of users during the day. Accordingly, a tanning booth is needed that can provide a tan in less than eight minutes, yet is easy to install and clean.

SUMMARY OF THE INVENTION

In view of the foregoing, one object of the present invention is to provide a tanning booth that is able to provide a tan within eight minutes. Another object of the invention to provide a tanning booth having a design that is easy to transport and install. It is another object of the invention to provide a tanning booth that is not complex in structure and which can be manufactured at low cost but yet efficiently. It is another object of the invention to provide a tanning booth that has efficient cooling to enable tanning in less than eight minutes. It is yet another object of the invention to provide a tanning booth that has a removable floor section for ease of cleaning beneath the booth.

In accordance with these and other objects, the tanning booth of the present invention generally has rectangular wall panels, a floor frame, a ceiling frame and a fan that is mounted to the ceiling. The wall panels are interconnected in the shape of a figure-8 in order to form a front section or room defined by front wall panels and a back section or room defined by back wall panels. In use, the front room is a changing area that provides privacy for the user to dress and undress, and the back room is the tanning area. An inside door is provided to separate the front room from the back room.

The front section and the back section are each hexagonal-shaped rooms that together form the rough figure-8 shape. Tanning lamps are provided to surround the user in the tanning room. The floor has a pattern of holes that permit air to be drawn through the tanning room by a fan mounted on the ceiling to sufficiently cool the user and lamps during tanning and enabling quicker tanning times.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENTS

Figure 4:
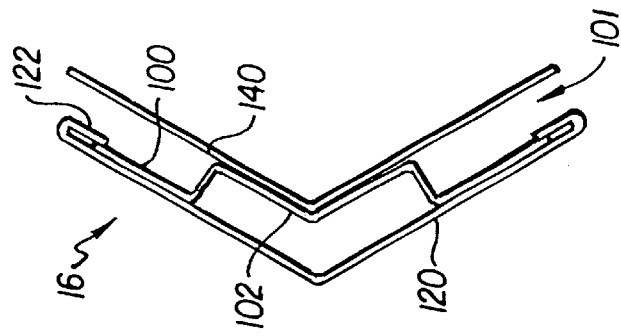
FIG. 4 is a cross-sectional view of the assembled inside corner post.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 1:
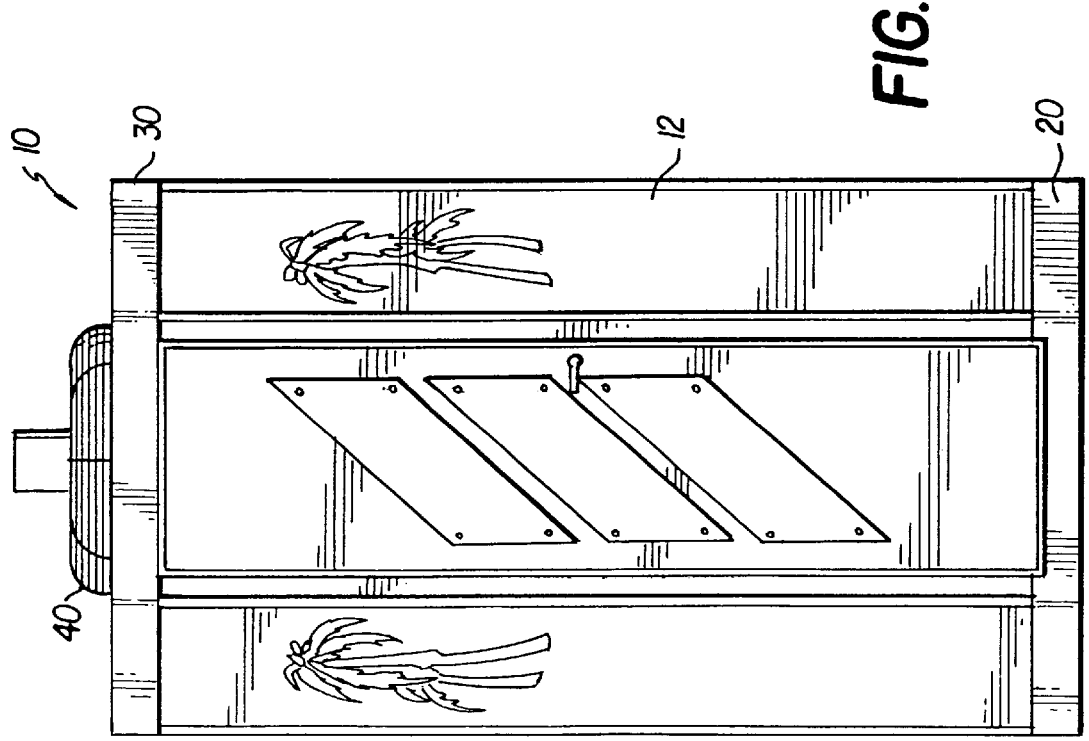
FIG. 1 shows a front plan view of the tanning booth in accordance with the preferred embodiment of the invention.
Figure 2:
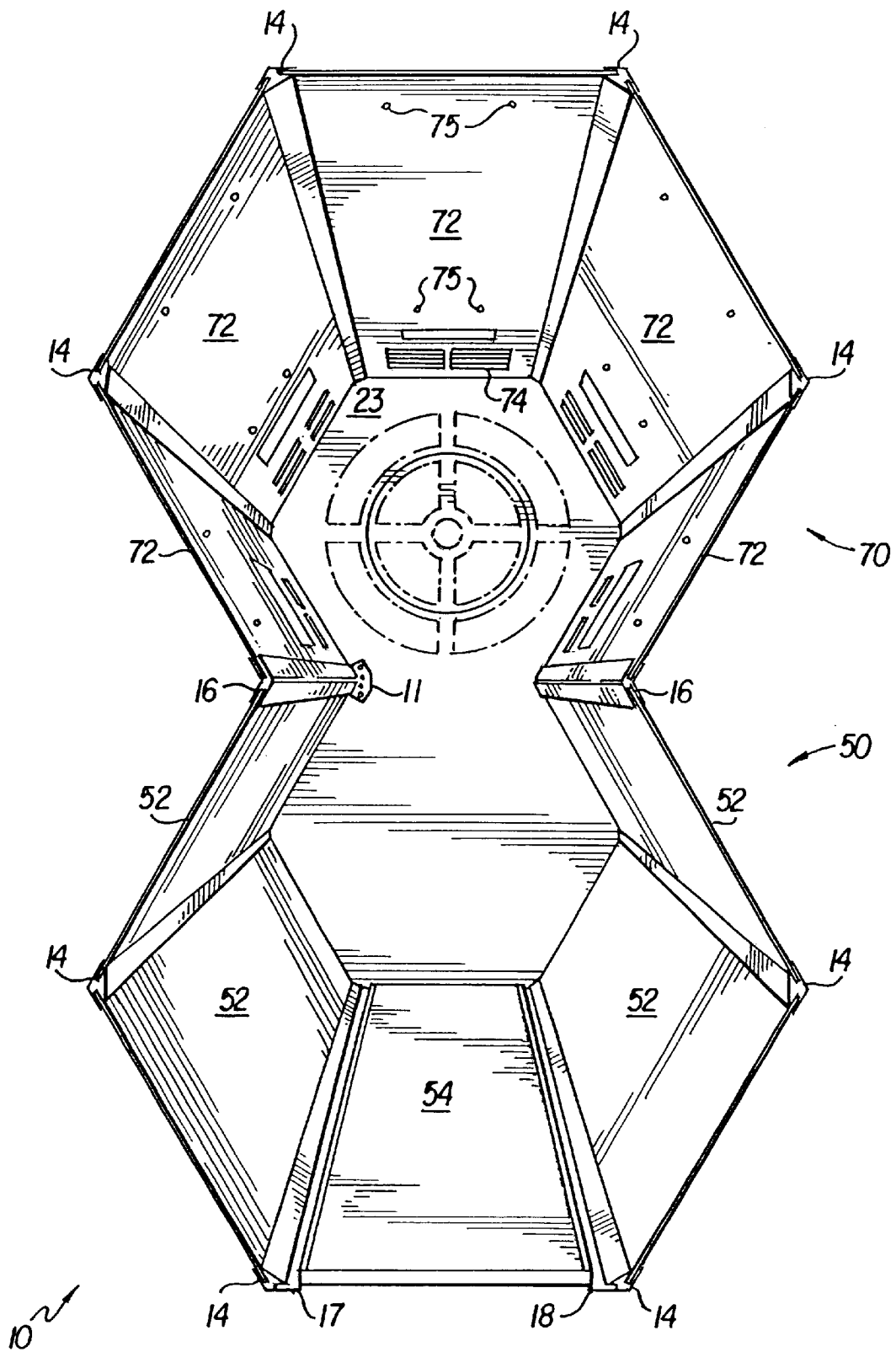
FIG. 2 is a top perspective view of the tanning booth, with the ceiling removed.
Figure 8:
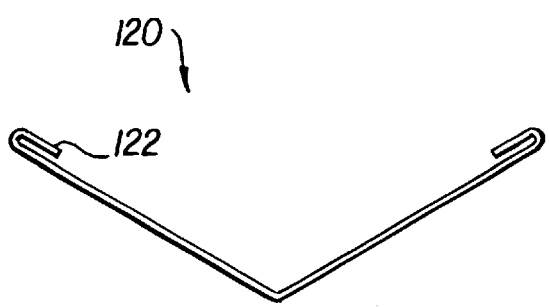
FIG. 8 is a cross-sectional view of the inside cover used with the inside corner post of FIG. 4.

Turning to the drawings, FIGS. 1 and 2 show an overall embodiment of the tanning booth 10 in accordance with the preferred embodiment of the invention. The tanning booth 10 generally has rectangular wall panels 12, a floor frame 20, a ceiling frame 30 and a fan 40 mounted to the ceiling. The wall panels 12 are interconnected in the shape of a figure-8 in order to form a front section or room 50 defined by front wall panels 52 and a back section or room 70 defined by back wall panels 72.

In use, the front room 50 is a changing area that provides privacy for the user to dress and undress, and the back room 70 is the tanning area. A hinge 11 is provided on the floor and ceiling to mount an inside door (See FIG. 8) that separates the front room 50 from the back room 70. One of the wall panels 54 of the front section 50 is a door 54 that allow ingress and egress to the interior of the tanning booth 10. The front section 50 and the back section 70 are each hexagonal-shaped rooms that together form the rough figure-8 shape.

The tanning booth 10 has a total of nine wall panels 12, plus the main door and an interior door. The five back wall panels 72 have ventilation ports or slots 74, whereas the front wall panels 52, including door 54, are solid. Outside corner posts 14 and inside corner posts 16 are provided to interconnect the wall panels 12 with one another. Each of the corner posts 14, 16 are formed by preassembled pieces. The inside corner posts 16 are "reverse bent" as compared to the outside corner posts 14.

The two outside corner posts 14 that are on either side of the front door 54 are formed as a hinge corner post 17 and a latch corner post 18. The hinge and latch corner posts 17, 18 are outside corner posts 14 that have a doorjamb built into them for the outside door 54 to be located on the front of the unit. The hinge corner post 17 has a hinge attached to the jamb and the latch corner post 18 has a latch hole predrilled into the jamb. The corner posts 14, 16 preferably extend the entire length of the tanning booth 10 to provide a more sturdy connection between the wall panels 12.

Figure 3:
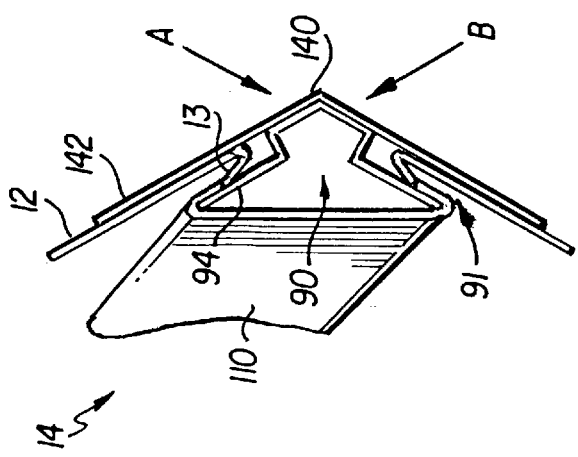
FIG. 3 is a perspective top view of the outside corner post assembled with the wall panels of the tanning booth and the inside and outside covers.
Figure 5:
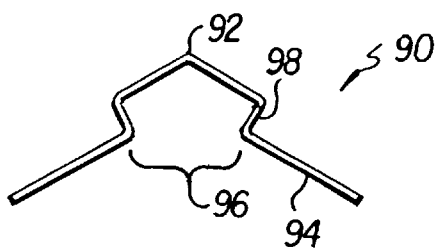
FIG. 5 is a cross-sectional view of the coupling member used with the outside corner of post of FIG. 3.
Figure 6:
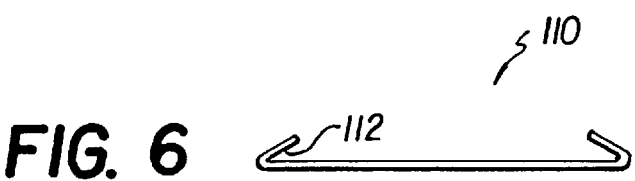
FIG. 6 is a cross-sectional view of the inside cover used with the inside corner post of FIG. 3.

FIG. 3 shows an assembled outside corner post 14 having a post member 140 and a coupling member 90. The coupling member 90 is welded to the post member 140 and a plastic inside cover 110 is connected to the coupling member 90. The coupling member 90, as best shown in FIG. 5, is bent at a mid-point 92 so that the arms 94 generally form a V-shape, with a mid-section 96 set back by legs 98. The post member 140 forms a general V-shape and has arms or ends 142 that can be bent inward to form fingers.

The post member 140 cooperates with the arms 94 and the legs 98 of the coupling member 90 to form a channel 91 that receives wall panels 12. The wall panel 12 has an inwardly-turned hem 13 that forms a snap-fit with the channel 91. During assembly, the wall panel 12 is pressed into the channel 91 by striking the corner post 140 at points A and B, such as with a hammer, a hand, or the like. The hem 13 is retained in channel 91 by the friction fit, as well as by the fingers 112 of the inside cover 110. The fingers 142 of the post member 140 push against the wall panel 12 to improve the friction fit. However, the fingers need not be provided and the post member 140 can instead have straight ends 142, as shown for the post member 140 in FIGS. 3 and 4.

FIG. 4 shows an assembled inside corner post 16 having a post member 140 and a reverse-bent coupling member 100. The coupling member 100 is welded to the post member 140 and a plastic inside cover 120 is connected to the coupling member 90. In contrast to the outside corner post 14, which positioned the post member 140 at the outside of the tanning booth 10, the inside corner post 16 positions the post member 140 at the inside of the tanning booth 10.

Figure 7:
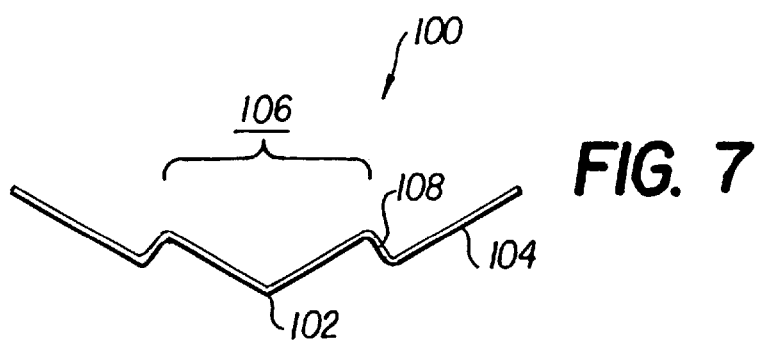
FIG. 7 is a cross-sectional view of the reverse-bent coupling member used with the inside corner post of FIG. 4.

Turning momentarily to FIG. 7, the reverse-bend coupling member 100 has a reverse bend at the mid-point 102 so that arms 104 generally form a wide-angled V-shape. The mid-section 106 is set forward by legs 108. As shown in FIG. 4, the arms 104 and the legs 108 cooperate with the post member 140 to form a channel 101 for receiving the wall panels 12 that are being connected together. The wall panel 12 is pressed into the channel 101, so that the hem 13 of the wall panel 12 forms a friction fit in the channel 101. The legs 98, 108 of the corner posts 14, 16 also function as a stop against which the wall panel 12 cannot be further inserted into the channel 91, 101.

The inside covers 110 are pieces that are placed in the area of the corner post 14, 16, at the inside of the booth 10 to conceal sharp edges and provide more rounded corners. Thus, the inside covers 110, 120, prevent injury to the user that might otherwise result from contact with the corner post 14. The inside cover 110 of the outside corner post 14 slides down over the ends of the arms 94 of the coupling member 90. Likewise, the inside cover 120 of the inside corner post 16 slides down over the ends of the arms 104 of the coupling member 100. The inside covers 110, 120 are preferably preassembled prior to the corner posts 14, 16 being connected to the wall panels 12, though can also be assembled after the wall panels 12 are connected. The inside covers 110, 120 are metal.

Figure 9:
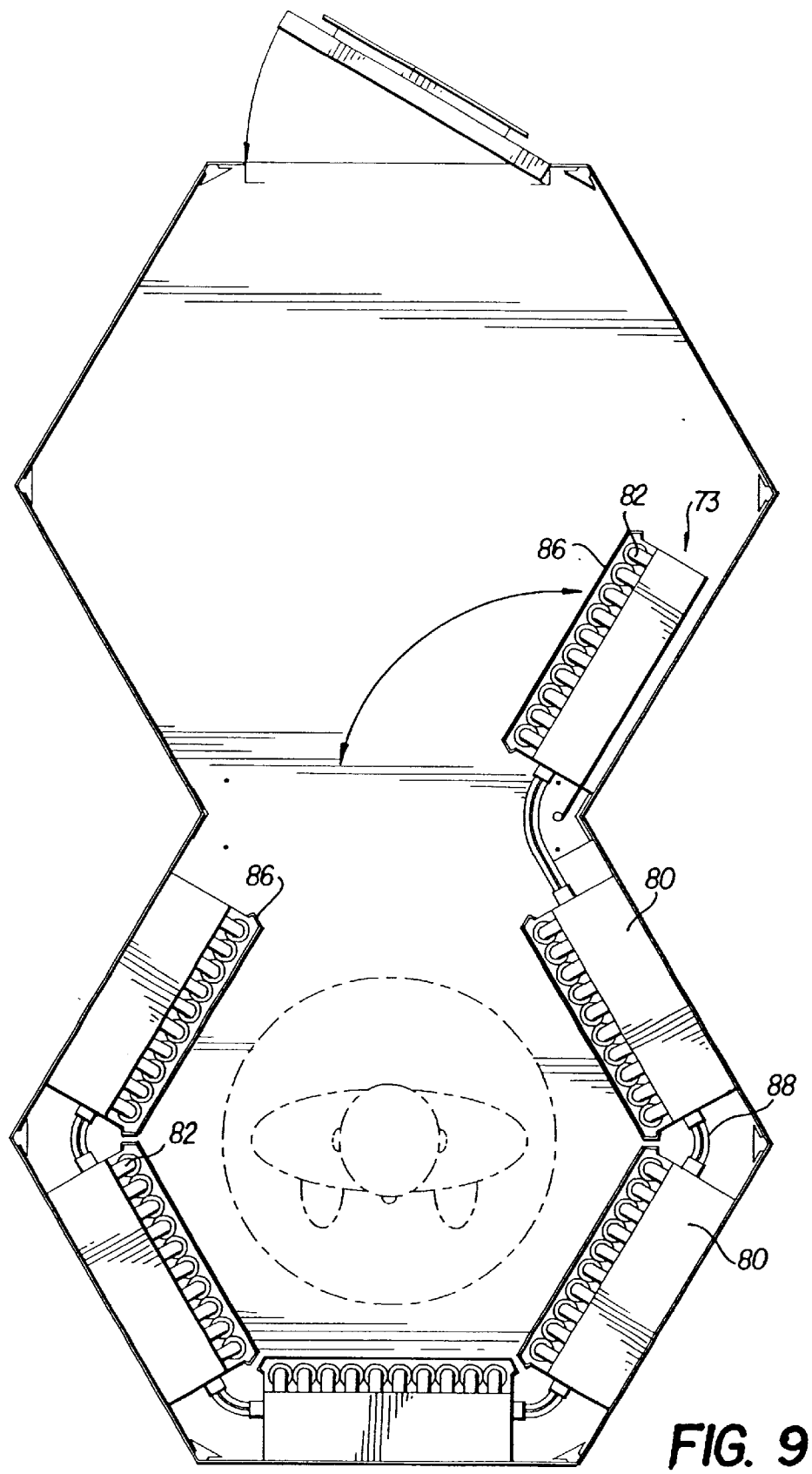
FIG. 9 is a top view of the tanning booth with lamp panels and lamps, with the ceiling removed.

Referring now to FIG. 9, the tanning booth 10 is shown with lamp panels 80 secured to the back wall panels 72. The back wall panels 72 and inside door 73 have fasteners or mounting screws 75 that engage respective openings on the rear of lamp panels 80 so that the lamp panel 80 hangs from the back wall panel 72. The lamp panels 80 are removably secured for ease of installation as well as repair and replacement.

Each lamp panel 80 has ten (10) tanning lamps 82, such that 60 tanning lamps 82 surround a user standing in the middle of the tanning room 70. The lamps 82 are approximately 71 inches in length and are positioned by the lamp panel 80 to be about 3 inches from the floor of the booth 10, so that the user receives an even full-body tan from head to toe. In addition, the lamps 82 are positioned to surround the user and provide an even disbursement of ultraviolet light 360° about the user, though preferably the user is directed to stand with his/her heels on the centerline of the floor pattern so that the user is in the center of all the lamps 82. Each lamp panel 80 has two 10- or 12-amp reset breakers that de-activate the lamps 82 of that panel 80 in the event of overheating.

Figure 10:
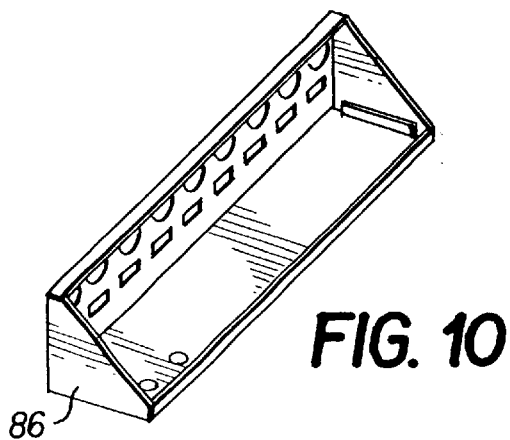
FIG. 10 is a perspective view of a lamp support for use with the lamp panel.

Support brackets 86 are located at the top, bottom and at about the middle of the lamp panel 80 to secure the lamps 82 to the lamp panel 80. The support bracket 86 prevents the lamps 82 from being removed from the lamp panel 80 and also reduce user contact with the lamps 82. The support brackets 86 have angled ends so that they do not interfere with one another when installed in the booth 10, as best shown in FIG. 9. As shown in FIG. 10, the support brackets 86 have round openings that receive a respective lamp 82.

The support brackets 86 are secured to the front of the lamp panel 80. A protective wire cage or guard (not shown) can also be secured to the support brackets 86. The wire cage preferably extends the length of the lamp panel 80 to provide a barrier between the user and the lamps 82, thereby preventing the user from coming into contact with the lamps 82. The wire cage can connect into the rectangular openings in the support bracket 86. Of course, any suitable number of support brackets 86 can be utilized with each lamp panel 80, or none at all.

Figure 11:
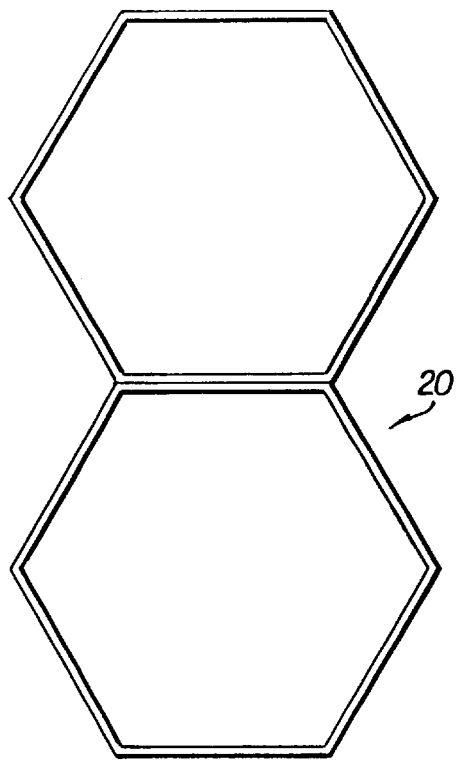
FIG. 11 is a top view of a floor frame used with the tanning booth.
Figure 12:
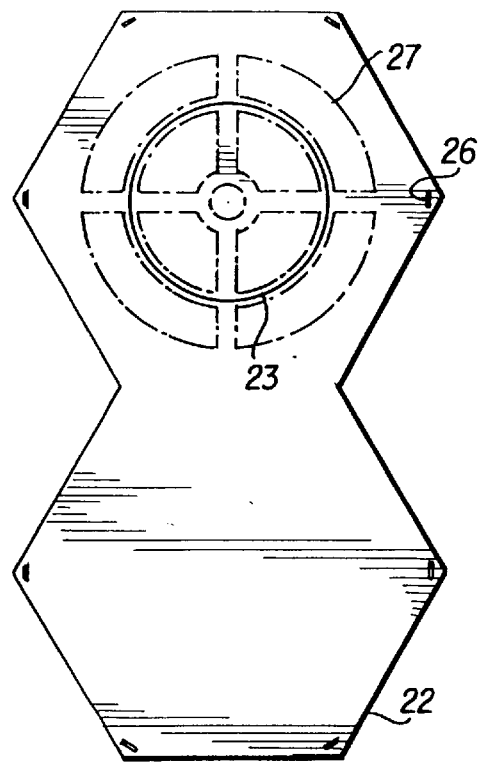
FIG. 12 is a top view of a floor used with the tanning booth.
Figure 15:
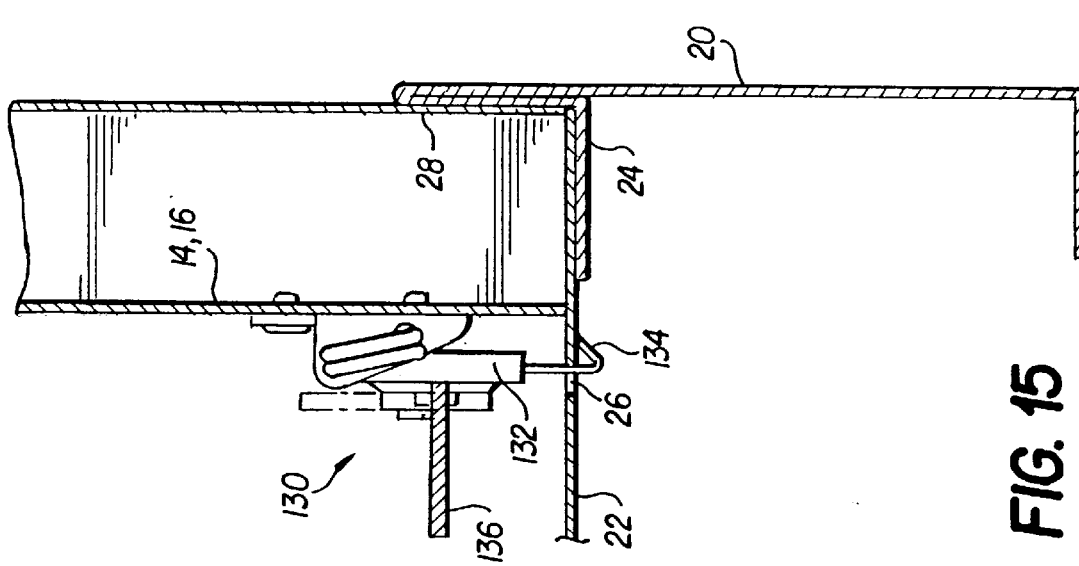
FIG. 15 is a cross-sectional side view of the corner post connected to the floor and floor frame.

Turning to FIG. 11, the floor frame 20 is shown as formed by two hexagonal members. The floor frame 20 supports a floor 22 (FIG. 12) that is placed onto the frame 20. As further shown in FIGS. 13 and 15, the floor frame 20 has a ledge 24 extending about the circumference of the frame 20 that supports the floor 22. The floor 22 has openings or slots 26 that are used to secure corner posts 14, 16. The ledge 24 is located at a distance from the top of the frame 20, to form a shoulder 28. The shoulder 28 provides support to the corner post 14, 16 and prevents the corner post 14, 16 from sliding off the floor 22. The floor 22 is removably connected to the floor frame 20, and the wall panels 12 and corner posts 14, 16 are removably connected to the floor 22.

The floor 22 has a circular mid-section 23 that is removable. The mid-section 23 has feet that support the user standing on the mid-section 23. The user can quickly and easily remove the mid-section 23 of the floor 22 in order to clean under the booth 10.

A fastener or latching mechanism 130 is fastened to the corner post 14, 16 by screws. The latch 130 has a hinge 132 having a hook 134 at one end. The hook 134 retracts to be out of the way when the post 14, 16 is being positioned on the floor 22. After the post 14, 16 is in position, the hinge 132 is rotated so that the hook 134 enters the opening 26 on the floor 22. The hook 134 retracts into the hinge 132 so that the hook 132 does not hit the floor 22 when being rotated into the opening 26.

A winged handle 136 is provided to enable the user to withdraw and extend the hook 134 into and out of the hinge. Accordingly, once the hinge is in position over the opening 26, the hook 134 is extended through the opening 26 to engage the underside of the floor 22. The winged handle 136 is then used to contract the hook 134, thereby securing the hook 134 and corner post 15, 16 to the floor 22. Though preferably only the corner posts 14, 16 are connected to the floor 22, the wall panels 12 may also be connected to the floor 22. In addition, one or all of the corner posts 14, 16 need not be connected to the floor 22.

Returning to FIG. 12, the floor 22 has a perforated hole pattern 27, and the floor frame 20 has vents. The hole pattern 27 and vents, as well as the vents 74 in the wall panels 72, permit air to flow from outside the booth 10 for effective cooling of the user. The pattern 27 is centered in the hexagonal room and has holes that are approximately 0.500 inches in diameter. The floor hole pattern 27 is circular with vertical and horizontal (in FIG. 12) solid supports that intersect a circular hole configuration in the center of the floor hole pattern 27. That design maximizes the number of holes that can be provided in the floor 22 while maintaining sufficient stability for the user.

Figure 14:
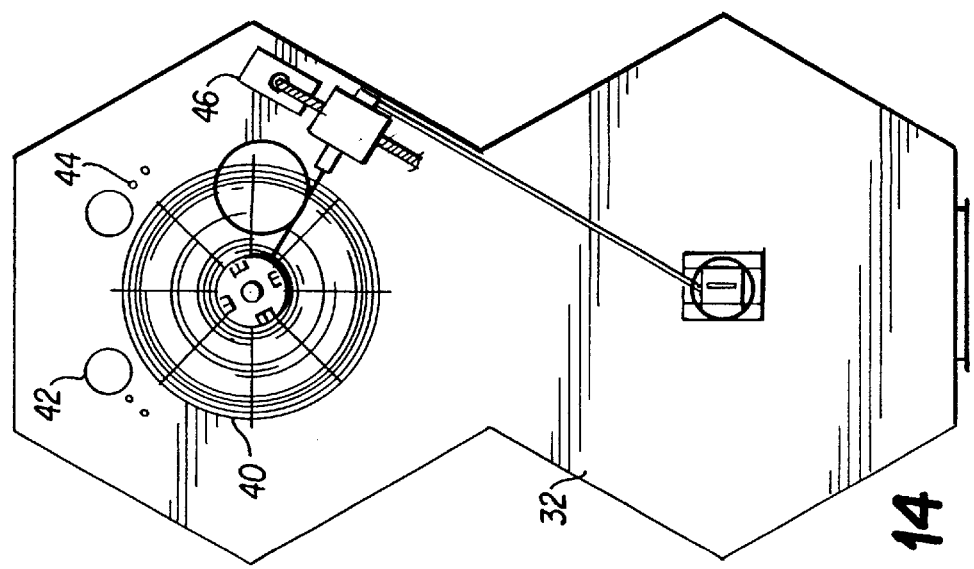
FIG. 14 is a top view of a ceiling having a fan used with the tanning booth.
Figure 13:
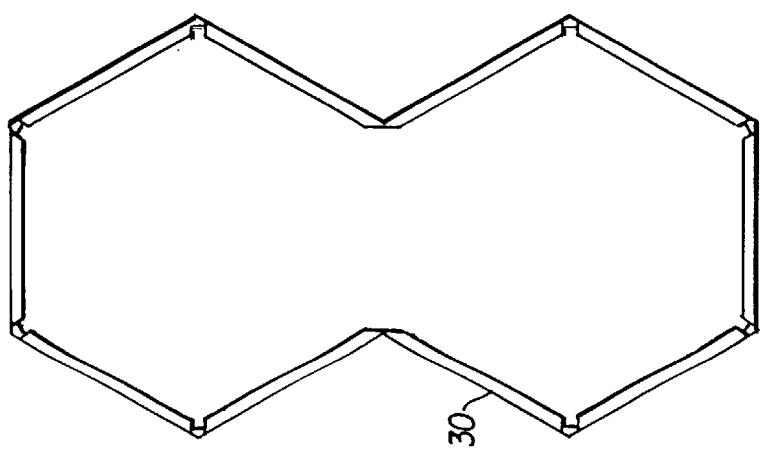
FIG. 13 is a top view of a ceiling frame used with the tanning booth.

As shown in FIG. 13, the ceiling frame 30 has a similar configuration to the floor frame 20. However, since the ceiling frame 30 does not support as much weight as the floor frame 20, the center support is not needed. Mounted to the top of the ceiling 32 (FIG. 14) is a fan 40, speakers 42, and an electrical access panel 46. The fan 40 can be used to draw air through the tanning booth room 70, which is drawn through the vents 74 in the wall panels 72, as well as the floor hole pattern 27 and vents in the floor frame 20.

Rope holes 44 are located in the ceiling 32. The rope holes 44 receive ropes that hang down into the tanning room 70. The user can hold onto the ropes to keep his/her arms raised for an all-around tan.

Figure 16:
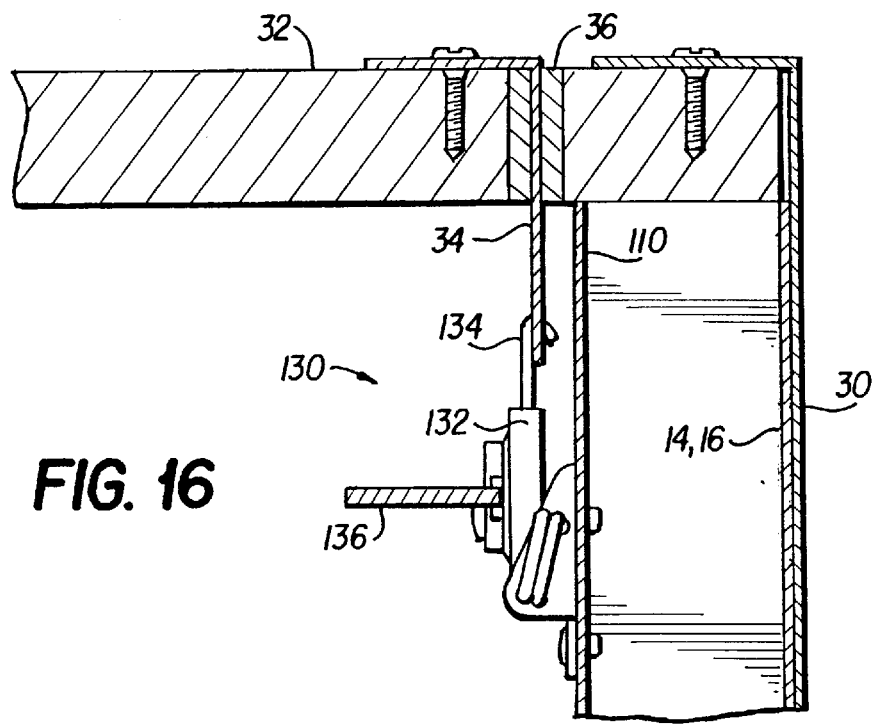
FIG. 16 is a cross-sectional side view of the corner post connected to the ceiling and ceiling frame; and, FIGS. 17 and 18 are circuit diagrams for controlling the tanning lamps and fan in accordance with the preferred embodiment.

Turning to FIG. 16, the ceiling 32 includes a right-angled bracket 34 that is secured to the top of the ceiling 32 and extends downward through an opening 36 in the ceiling 32 into the interior of the tanning booth 10. A latch 130 is secured to the cover 110 of corner post 14, 16. The hook 134 of the latch 130 engages an opening located in the bracket 34 to connect the corner post 14, 16 to the ceiling 32. The top frame 30 also forms a right angle that is secured to the ceiling 32 and extends downward to support the walls 12 and corner posts 14, 16.

The fan 40 and floor hole pattern 27 are important to provide sufficient cooling to the user due to the heat generated by the tanning lamps 82. The increased number and output of the lamps 82 require adequate cooling to ensure the comfort and safety of the user. The fan 40 and floor hole pattern 27 enable a quick tan time of between one minute (for people with sensitive skin that burn easily) and eight minutes (for people with dark skin that burn minimally) without danger to the user. However, the actual tan time also depends upon other conditions, such as the moisture condition of the skin. At least 3 inches of ventilation space should be provided all around the booth 10 to ensure adequate ventilation of the tanning room 70.

The tanning booth 10, including the wall panels 12, floor frame 20, floor 22 and ceiling frame 30 are constructed of steel and the booth 10 is easy to assemble. The ceiling 32 is preferably made of ¾ inch particle board with a plastic laminate to reduce the amount of noise and vibration that enters the tanning booth from the fan. The configuration and design of the tanning booth 10 establishes a safe distance from the user to the tanning lamps, but at the same time maintains maximum tanning effect.

The lamps have an output of 160 watts so that a quicker tan time of 4, 6 or 8 minutes is achieved. Accordingly, the lamps generate about 28.0 watts of UVA/UVB flux, for a total from the 60 lamps of about 1,680 watts/minute of ultraviolet radiation that enable a user to obtain a tan. As a result, each lamp generates about 10.2 BTU per minute of heat, which requires the blower to dissipate about 612 BTU of heat per minute in order to maintain a comfortable ambient temperature of less than 90 degrees in the tanning booth. It should be recognized that the number and output of the lamps is exemplary only, and is not intended to be limiting; the optimal number may be less or more than the number provided.

The tanning booth 10 is compact for easy shipping and delivery. The booth can be quickly installed for use by first assembling and positioning the floor frame 20. The floor 22 is then placed on the floor frame 20. The wall panels 12 are connected together by the various outside and inside corner posts 14, 16 into position on the flooring 22 and against shoulder 28. The corner posts 14, 16 are secured to the floor 22 by use of the twist latches 130. The ceiling frame 30 is assembled and placed over the wall panels 12 and posts 14, 16. The ceiling 32 is then positioned inside the ceiling frame 30 and secured to the wall panels 12 and posts 14, 16 by twist latches 130.

Once the floor 20, wall panels 12, posts 14, 16 and ceiling 30 are assembled, the doors 54, 73 can be installed. The lamp panels 80 are hung on the wall panels 72 and door 73 and connected with cable 88. The tanning lamps are activated by a timing switch that also activates the fan 40.

Figure 17A:
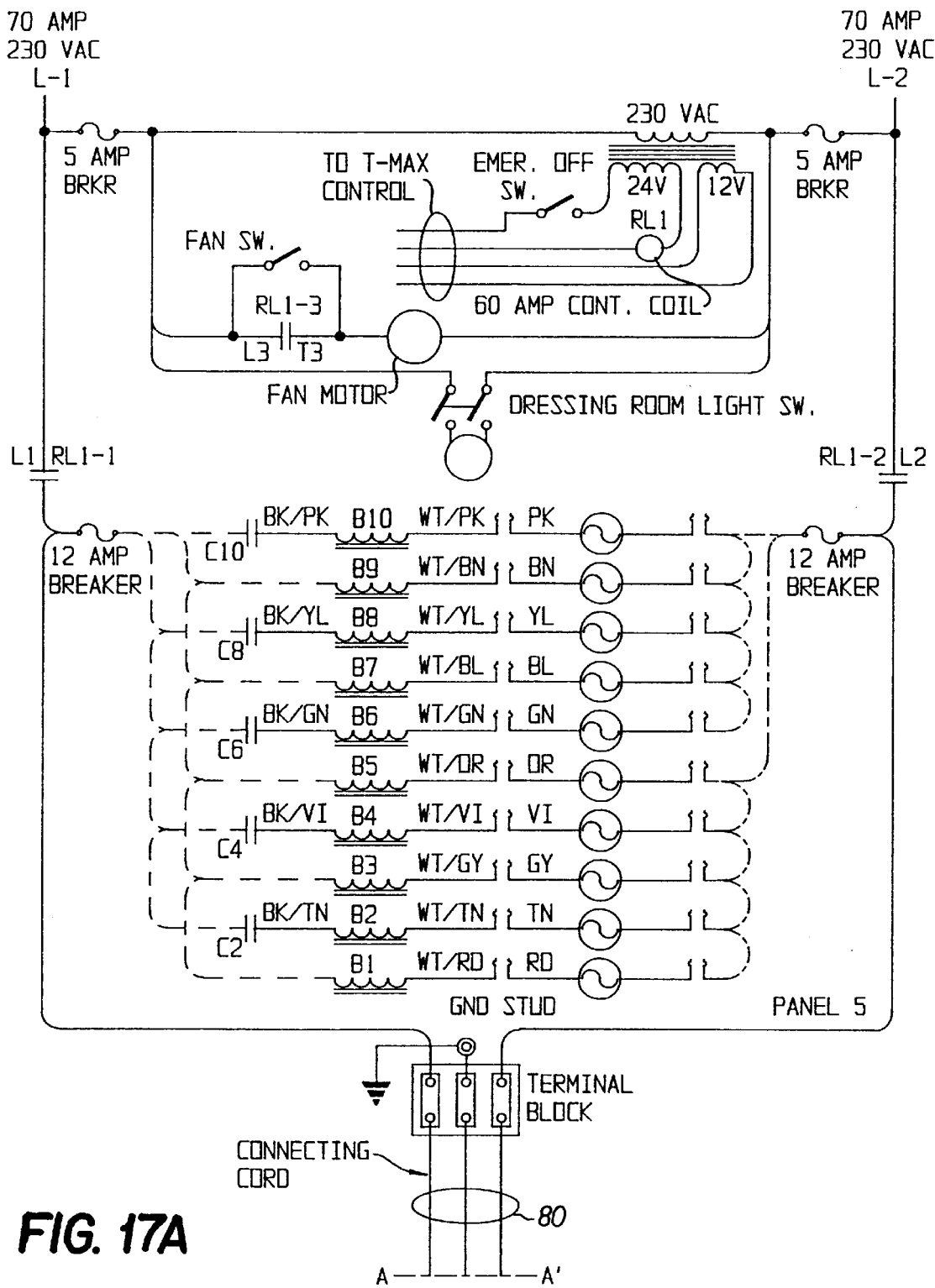
Figure 17B:
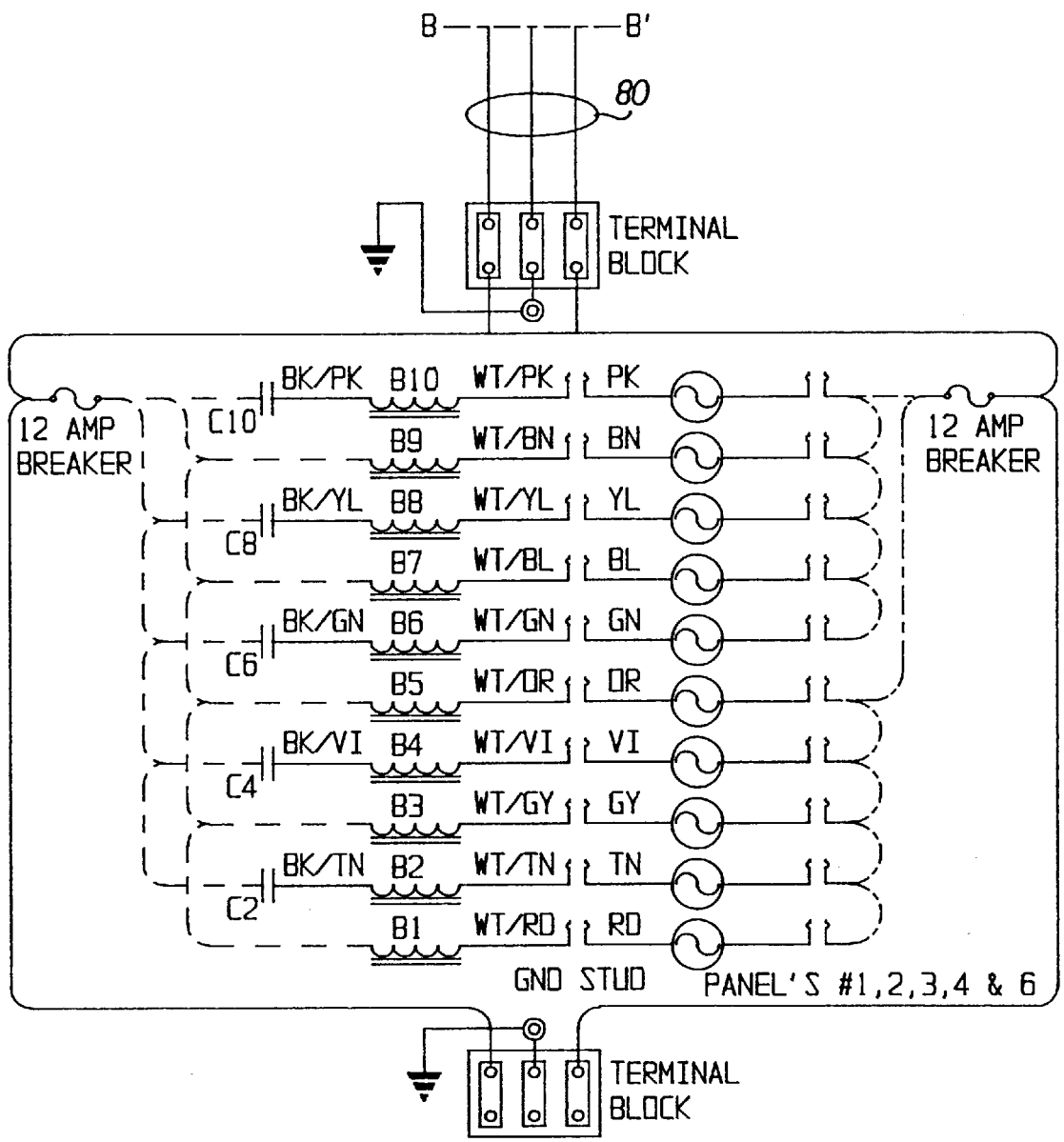
Figure 18:
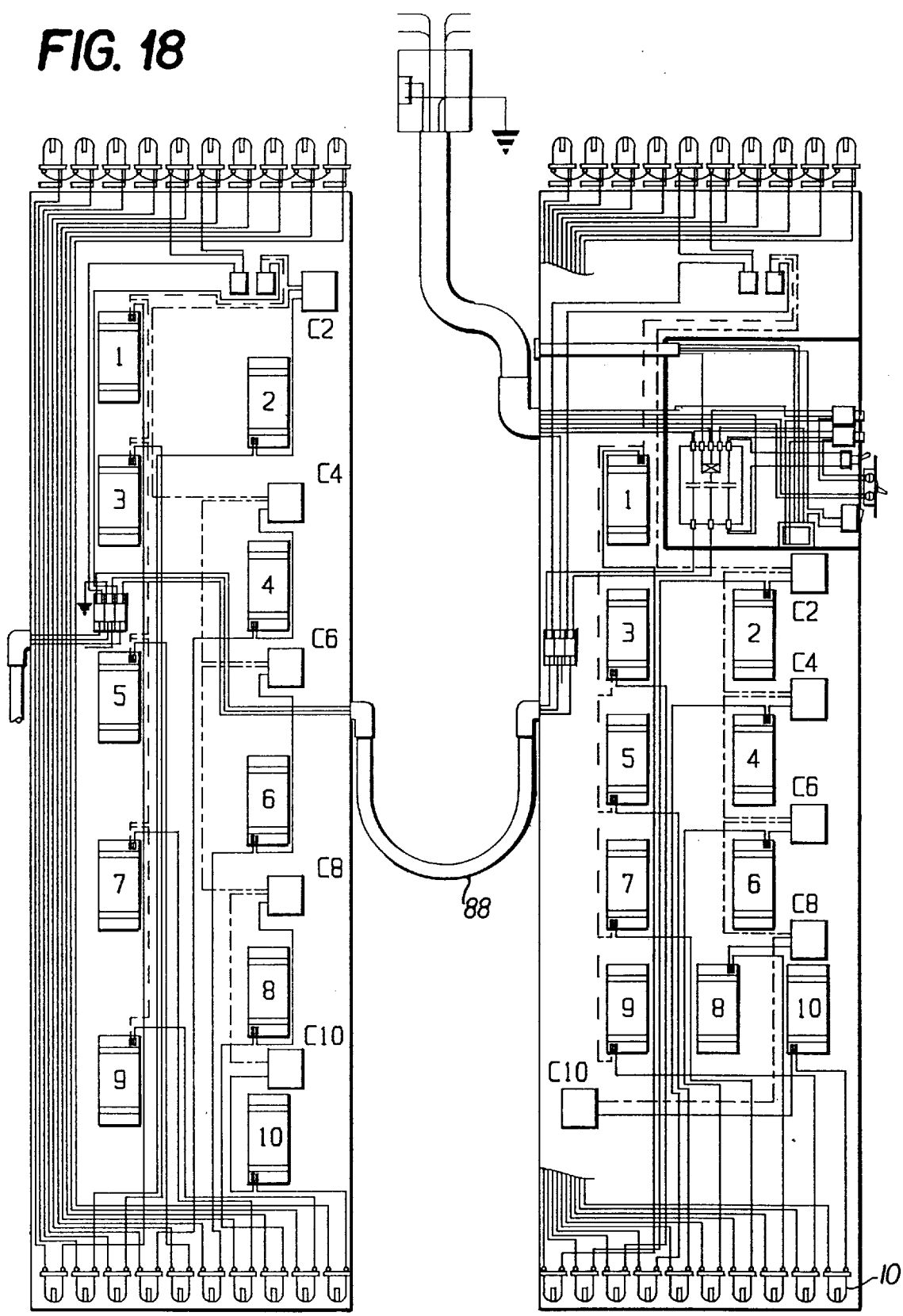

Referring to FIGS. 17 and 18, the lamp panels 80 are connected to each other by a removable connecting cord 88, as also shown in FIG. 9. Preferably, between about 7–10 lamps are provided in a vertical, side-by-side manner. There is a dual output control transformer that provides power to a timer that can be set by the user prior to entering the tanning room 70. The transformer has two outputs, a first output is a 24 volt used to power the starting contact and a 12 volt output for the timer. The starting contact is a relay switch used to bring the main power online. The timer is programmed to time out after a period of time. The timer is controlled by a store attendant via a processor located outside of the booth.

The foregoing description and drawings should be considered as illustrative only of the principles of the invention. The invention may be configured in a variety of shapes and sizes and is not limited by the dimensions of the preferred embodiment. Numerous applications of the present invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

I claim:

1. A tanning booth for imparting a tan to a user, the tanning booth comprising:

a floor for receiving the user, said floor having a plurality of openings in substantially close proximity to one another to forming a ventilation pattern that permits air flow, the ventilation pattern defining a user position such that the ventilation pattern is directly surrounding the user;

at least one wall panel located about said floor, wherein said at least one wall panel defines a tanning area about the user position;

a ceiling having a ventilation opening; and, a blower secured to said ceiling and positioned in the ventilation opening to direct an air flow through the tanning area and the ventilation pattern.

2. The tanning booth of claim 1, further comprising at least one lamp assembly connected to said at least one wall panel and positioned about the tanning area to project the generated tanning rays into the tanning area, wherein each of said at least one lamp assembly has ten lamps.

3. The tanning booth of claim 1, further comprising at least one lamp assembly connected to said at least one wall panel and positioned about the tanning area to project the generated tanning rays into the tanning area, wherein said at least one lamp assembly generates 1,680 watts per minute of ultraviolet radiation.

4. The tanning booth of claim 1, further comprising at least one lamp assembly connected to said at least one wall panel and positioned about the tanning area to project the generated tanning rays into the tanning area, wherein said at least one lamp assembly generates sufficient ultraviolet radiation to provide a tan within about eight minutes.

5. The tanning booth of claim 1, wherein said blower and the ventilation pattern dissipate at least 500 BTU of heat per minute.

6. The tanning booth of claim 1, wherein the tanning booth has a hexagonal shape.

7. The tanning booth of claim 1, wherein said wall panel is a door.

8. The tanning booth of claim 1, wherein the tanning booth has a figure-8 shape defining the tanning area and a changing area.

9. The tanning booth of claim 1, further comprising a corner post for connected to said floor and engaging said wall panel, wherein said corner post has a post member with at least one arm forming a general V-shape and a coupling member having at least one arm, said coupling member connected to said post member so that the at least one arm of said coupling member is parallel to and separated from the at least one arm of said post member to form a channel therebetween, the channel receiving said wall panel for connecting said corner post to the received wall panel.

10. The tanning booth of claim 9, said coupling member having at least one leg continuous with the at least one arm, the at least one leg separating the at least one arm of said coupling member from the at least one arm of said post member and providing a stop in the channel against which the received wall panel cannot be further inserted into the channel.

11. The tanning booth of claim 9, further comprising a cover removably connected to said coupling member.

12. A tanning booth for imparting a tan to a user, the tanning booth comprising:

a floor frame having at least one opening that permits air flow;

a floor located on said floor frame, said floor having a plurality of openings that permits air flow, said floor having a center portion for receiving a user of the tanning booth, and wherein the plurality of openings are substantially located in the center portion of said floor;

at least one wall panel located about said floor frame and defining a tanning area which receives the user;

a ceiling having a ventilation opening; and, a blower secured to said ceiling and positioned in the ventilation opening to direct an air flow through the tanning area, the ventilation pattern and the at least one opening in said floor frame.

13. The tanning booth of claim 12, further comprising a corner post secured to said floor and engaged with adjacent wall panels, and a fastener connected to at least one of said corner posts for removably securing said at least one corner post to said floor.

14. The tanning booth of claim 13, said fastener having a hook and said floor having an opening, wherein the hook of said fastener removably engages the opening in said floor.

15. The tanning booth of claim 12, further comprising a corner post secured to said floor and engaged with adjacent wall panels, and a fastener connected to at least one of said corner posts for removably securing said at least one corner post to said ceiling.

16. The tanning booth of claim 15, further comprising a bracket connected to said ceiling, said fastener having a hook for removably engaging said bracket.

17. The tanning booth of claim 1, wherein a section of said floor is removable to permit access to beneath said floor.

18. The tanning booth of claim 12, said floor frame having a ledge extending inwardly about the perimeter of said floor frame for receiving said floor, said ledge defining a side portion of said floor frame, wherein the wall panels rest against the side portion of said floor frame when the wall panels are located about said floor.

19. The tanning booth of claim 12, further comprising a corner post secured to said floor and engaged with adjacent wall panels, and a ceiling frame connected to said ceiling for retaining said corner posts.

20. The tanning booth of claim 19, said ceiling frame comprising a right-angled bracket.

21. The tanning booth of claim 12, further comprising a ceiling frame connected to said ceiling for retaining said at least one wall panel.

22. The tanning booth of claim 1, wherein the ventilation pattern is substantially located at a center of said floor.

23. The tanning booth of claim 1, wherein the ventilation opening is substantially located at a center of said ceiling.

24. The tanning booth of claim 23, wherein the ventilation opening is substantially located at a center of said ceiling.

25. A tanning booth for imparting a tan to a user, the tanning booth comprising:

a floor frame having at least one opening that permits air flow;

a floor located on said floor frame, said floor having a plurality of openings in substantially close proximity to one another and permit air flow;

at least one wall panel located about said floor frame, said at least one wall panel defining a tanning area which receives the user;

a ceiling having a ventilation opening located substantially in a center of said ceiling; and, a blower secured to said ceiling and positioned in the ventilation opening to direct an air flow through the tanning area, the ventilation and the at least one opening in said floor frame.

26. The tanning booth of claim 25, wherein the ventilation pattern is substantially located at a center of said floor.

27. A tanning booth comprising a floor, wall panels located about said floor to define a tanning area, and at least one corner post connected to adjacent wall panels, said at least one corner post having a post member with at least one arm forming a general V-shape and a coupling member having at least one arm, said coupling member connected to said post member so that the at least one arm of said coupling member is substantially parallel to and separated from the at least one arm of said post member to form a channel therebetween, the channel receiving one of said wall panels for engaging said corner post to the received wall panel.

28. The tanning booth of claim 27, said coupling member having at least one leg continuous with the at least one arm, the at least one leg separating the at least one arm of said coupling member from the at least one arm of said post member and providing a stop in the channel against which the received wall panel cannot be further inserted into the channel.

29. The tanning booth of claim 27, further comprising a cover removably connected to said coupling member.

30. A booth comprising at least one wall defining a receiving area for receiving a user, the booth comprising a floor having a plurality of openings that permit air flow, said plurality of openings positioned directly about the user to define a user position within the receiving area, a ceiling having a ventilation opening, and a blower secured to said ceiling and positioned in the ventilation opening to direct an air flow through the plurality of openings and directly past the user to contact the user.

31. The tanning both of claim 1, further comprising at least one lamp assembly connected to at least one of said at least one wall panel and positioned about the user position to project tanning rays into the user position.

32. The tanning booth of claim 1, wherein air flows through the plurality of openings of the ventilation pattern substantially unhindered.

33. The tanning booth of claim 12, further comprising at least one lamp assembly connected to at least one of said at least one wall panel to project tanning rays into the tanning area.

34. The tanning booth of claim 12, wherein air flows through the plurality of openings substantially unhindered.

* * * * *